United States Patent
Wang et al.

(10) Patent No.: US 9,874,557 B2
(45) Date of Patent: Jan. 23, 2018

(54) PROGRESSIVE COMPRESSION DRIVEN FLOW CARTRIDGE FOR ANALYTE DETECTING STRIP AND METHOD

(71) Applicant: DNT SCIENTIFIC RESEARCH, LLC, San Diego, CA (US)

(72) Inventors: Naishu Wang, San Diego, CA (US); David F. Zhou, San Diego, CA (US)

(73) Assignee: DNT Scientific Research, LLC, San Diego, CA (US)

( * ) Notice: Subject to any disclaimer, the term of this patent is extended or adjusted under 35 U.S.C. 154(b) by 74 days.

(21) Appl. No.: 15/188,859

(22) Filed: Jun. 21, 2016

(65) Prior Publication Data
US 2017/0108498 A1    Apr. 20, 2017

Related U.S. Application Data

(63) Continuation of application No. 14/887,179, filed on Oct. 19, 2015, now Pat. No. 9,377,457.

(51) Int. Cl.
*G01N 21/75* (2006.01)
*G01N 33/543* (2006.01)
*G01N 33/569* (2006.01)

(52) U.S. Cl.
CPC . *G01N 33/54386* (2013.01); *G01N 33/56983* (2013.01)

(58) Field of Classification Search
CPC .................. G01N 33/54386; G01N 33/56983
See application file for complete search history.

(56) References Cited

U.S. PATENT DOCUMENTS

| 5,622,871 A | 4/1997 | May et al. |
| 5,843,691 A | 12/1998 | Douglas et al. |
| 6,140,136 A | 10/2000 | Lee |
| 7,932,099 B2 | 4/2011 | Egan et al. |
| 2004/0247487 A1 | 12/2004 | Commercon et al. |
| 2005/0227370 A1* | 10/2005 | Ramel ...................... C12Q 1/00 436/514 |

(Continued)

OTHER PUBLICATIONS

USPTO, International Search Report PCT/US2016/057761, dated Jan. 10, 2017.

*Primary Examiner* — Dennis White
(74) *Attorney, Agent, or Firm* — Charmasson, Buchaca & Leach, LLP

(57) ABSTRACT

A cartridge and method for conducting a labeled molecular affinity binding test such as antibody/antigen, ligand/receptor, and colorometric reactions, and other chemical reactions for which one or more analytes is present in a liquid sample formate. A progressive compression structure progressively forces a liquid flow out of a conjugate pad toward a reaction region to more thoroughly and rapidly mix the liquid, encouraging specific first affinity binding to the analytes in question. A specially dimensioned constricting passageway surrounding the reaction region including the result zones provides an additional siphoning force to the flow. These combined forces rapidly and more evenly guide the flow of liquid through the reaction region so that the rushed rate of uptake of analytes at the strip lines are more evenly distributed, adhesive attachment of non-specific molecules is largely avoided, vastly improving sensitivity and specificity, and providing quantitative results in some tests.

20 Claims, 6 Drawing Sheets

(56) References Cited

U.S. PATENT DOCUMENTS

| | | |
|---|---|---|
| 2009/0289201 A1 | 11/2009 | Babu et al. |
| 2011/0081641 A1 | 4/2011 | Gould |
| 2014/0242613 A1* | 8/2014 | Takeuchi ......... G01N 33/54393 |
| | | 435/7.32 |

* cited by examiner

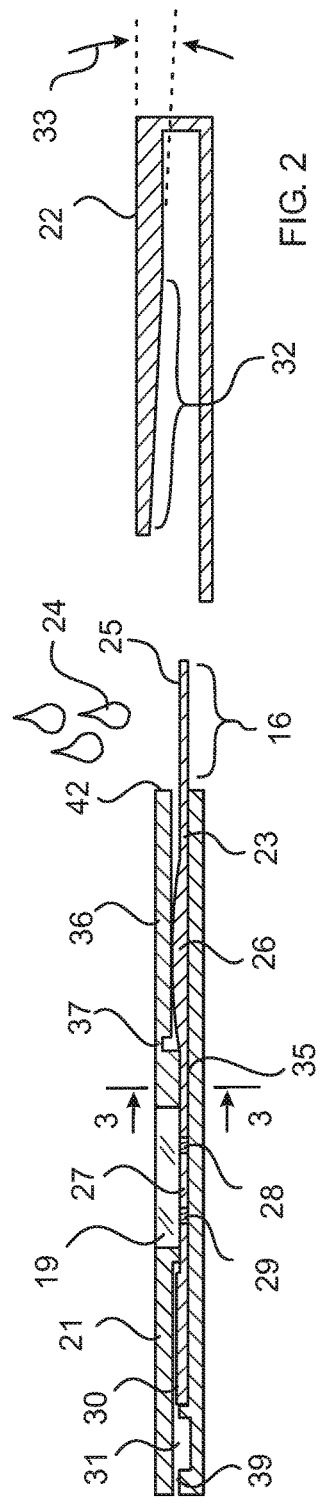

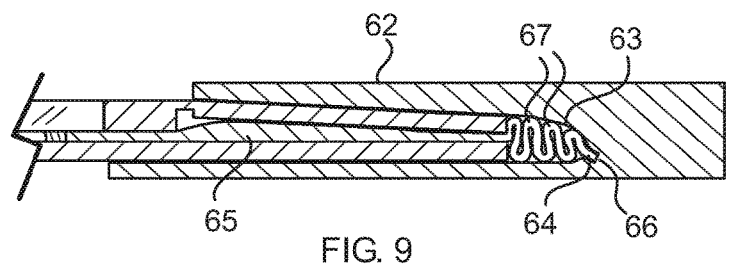
FIG. 9
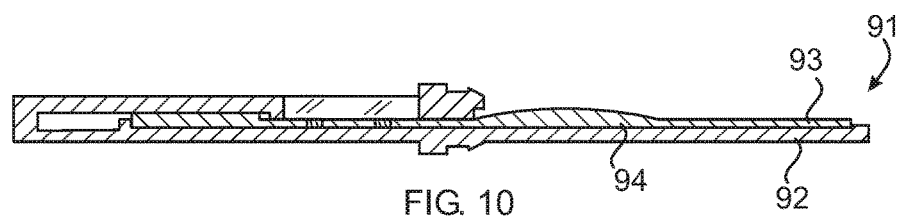
FIG. 10
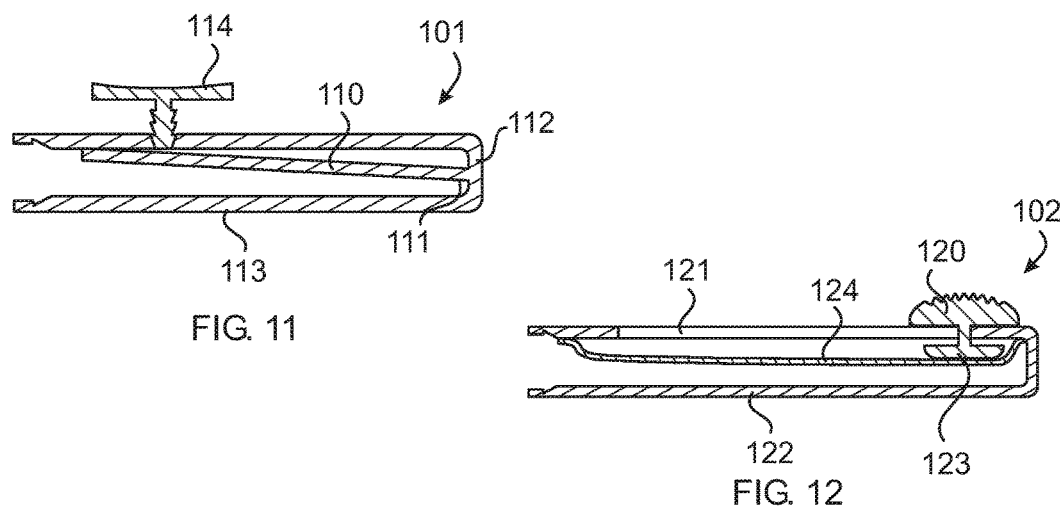
FIG. 11
FIG. 12
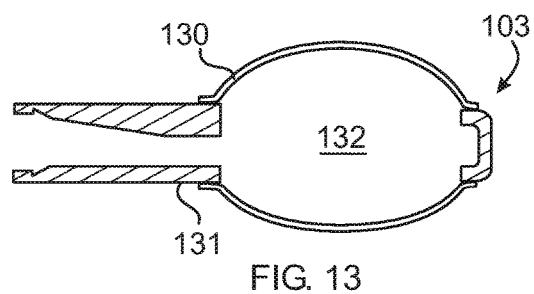
FIG. 13

PROGRESSIVE COMPRESSION DRIVEN FLOW CARTRIDGE FOR ANALYTE DETECTING STRIP AND METHOD

PRIOR APPLICATION

This is a continuation of U.S. patent application Ser. No. 14/887,179, filed 2015 Oct. 19, now U.S. Pat. No. 9,377,457, issued 2016 Jun. 28.

FIELD OF THE INVENTION

This invention relates to apparatuses for analyzing liquids such as some body fluids using labeled molecular affinity binding, such as immunochromatography, and more particularly to strip test apparatuses for detecting an analyte such as an antibody or antigen which may indicate a particular condition.

BACKGROUND

Labeled molecular affinity binding such as immunochromatographic assays have existed for decades and have proven to be an inexpensive way to screen for various conditions such as abused drugs and other conditions such as pregnancy, cancer, or for single or multiple pathogenic conditions such as HIV infection.

In the point-of-care test (POCT) setting, immunochromatographic assays are typical conducted using lateral flow strip technology as described in May et al., U.S. Pat. No. 5,656,503 incorporated herein by reference. Unfortunately, although they can be fast, inexpensive, and simple-to-use, depending on the type of condition being detected, these tests provide a typical accuracy of between 75% and 95%, falling short of the 99% or above accuracy generally considered to be necessary for a confirmatory test, and providing no objective measure of a quantitative result, i.e. the concentration of a given drug present in the liquid being tested.

The reasons for the insufficient accuracy in many rapid IVD test devices are primarily due to their current lack of overall higher sensitivity and specificity. Different samples may contain chemicals or particles which inhibit the rapid and well mixed liquid flow or otherwise interfere with one or both of the first and second affinity binding reactions.

Some devices such as our improved accuracy devices disclosed in our U.S. Pat. No. 8,021,625 (Wang et al.) incorporated herein by reference, may not be sufficiently compact or inexpensive to use in the field.

Other prior devices have attempted to enhance sensitivity or specificity by pretreating various parts of the device with reaction or flow enhancing reagents, pH conditioning chemicals, or even non-specific adhesive blocking molecules which will "block-out" non-analyte molecules which might cause non-specific adhesion, or otherwise compete with the analyte in question for specific binding members, especially in the reaction zones region of the strip. These attempts have met with limited success in some types of testing, but do not provide the desired accuracy in many others. Also, pretreatment with two or more of the above pretreatments exacerbates the difficulties in obtaining uniform manufacturing due to potential incompatibilities between the pretreatment chemicals. For example, the pH conditioner might disrupt the effectiveness of the non-specific blocking member molecules. Or, the manufacturing step of pretreating with the second pretreatment chemical can dislodge some of the first pretreatment chemical.

Further, lot-to-lot variation in the manufacture of many IVD test devices can often lead to ambiguous results, such as false negatives as well as weak false positives, so-called "ghost lines" or "phantom lines". False negatives typically occur when non-specific molecules interfere with the first and/or second affinity binding actions. It has been found that non-analyte molecules can clump together in liquid samples that are not well mixed so that they temporarily prevent access between analytes and binding members. Even temporary interference in past devices can prevent an adequate number of labeled analyte complexes and/or ultimately immuno-sandwich complexes from forming. In this way, if a non-analyte molecule or clump of molecules blocks access between analytes and binding members for only a few seconds, it may be enough to induce a false negative result. Further, clumps of non-analyte molecules can carry an overabundance of the labeled mobilizable binding members to the second affinity binding site to generate a false positive result.

One area of recent improvement in rapid diagnostic testing involves using the capabilities offered by mobile communication devices such as smart phones. As disclosed in Ozcan et al., U.S. Pat. No. 8,916,390, incorporated herein by reference, a lateral flow-type strip can be automatedly scanned by the camera of a smart phone which can be interpreted by software to obtain a result and deliver it to a wireless network. Lateral flow devices are useful due to their low cost and ease of use. However, prior lateral flow devices suffer from low accuracy as detailed above. This is especially true for saliva testing because of the low concentrations of analytes present. Current lateral flow strips cannot provide the necessary sensitivity and specificity within the time normally allotted to a typical law enforcement action such as a traffic stop.

The low accuracy can be due to a number of problems unique to lateral flow-type tests. First, there is often uneven movement of the immunoparticles within the nitrocellulose membrane. Smaller, non-analyte molecules mixed together with the larger analyte molecules and compete for sites and often prevent the larger molecules from reacting in the desired fashion.

Therefore, there is a need to improve the accuracy of rapid IVD test devices so that rapid inexpensive easily conducted quantitative immunological testing becomes a reality.

SUMMARY

The principal and secondary objects of the invention are to provide an improved molecular affinity binding assay strip device for visual or automated reading exhibiting rapid results.

These and other objects are achieved by a strip-carrying cartridge having a progressive compression structure for driving a high speed flow of liquid in the strip.

In some embodiments the results can be rapid qualitative/quantitative results with up to 99.9% accuracy.

In some embodiments the compression structure causes a high speed rapid flow of liquid out of a conjugate pad toward a reaction region.

In some embodiments the compression structure causes a high speed rapid flow of liquid out of a sample collect pad and then a conjugate pad toward a reaction region.

In some embodiments there is provided a labeled molecular affinity binding assay strip device having a source of mobilizable first affinity binding members in the conjugate pad and a number of fixed second affinity binding sites in the reaction region.

In some embodiments there is provided a more predictable rate of uptake of labeled analytes at the strip lines in order to provide a quantitative result.

In some embodiments there is a strip-surrounding constriction structure including the surface of the reaction zones of the test strip providing a siphoning force component to the liquid flow.

In some embodiments there is provided a device for testing a liquid sample for the concentration of at least one analyte, wherein said device comprises: at least one test strip comprising: at least one sample pad; at least one conjugate pad including a source of mobilizable labeled first affinity binding members bindable to said analyte; and, a liquid permeable reaction region including at least one result zone including immobilized second affinity capture binding members bindable to said analyte; a cartridge body, made of liquid impermeable material, having an internal cavity shaped and dimensioned to carry a first portion of said strip including said at least one conjugate pad; an end cap shaped and dimensioned to engage said body, made of liquid impermeable material, having an internal chamber shaped and dimensioned to enclose a remainder portion of said strip including a section of said at least one sample pad; a survey window though said body for reading a status of said at least one result zone; wherein said body comprises a compression structure shaped, dimensioned and located to impart a compression force upon said conjugate pad.

In some embodiments said body further comprises a constriction passageway along a part of said reaction region including said at least one zone.

In some embodiments said constriction passageway is shaped and dimensioned to loosely contact an entire perimeter of a latitudinal cross-section of said strip, thereby creating a liquid siphoning region including said at least one zone.

In some embodiments said compression structure comprises a deflectable beam cantilevered over said conjugate pad.

In some embodiments said deflectable beam comprises a first end fixed to said body and a second opposite free end.

In some embodiments said end cap comprises an internal ramp structure oriented to bear against said beam and force progressive deflection of said beam toward said conjugate pad during movement of said cap from an open position to a closed position.

In some embodiments said compression force has a distal component and proximal component, downstream from said distal component, and wherein said distal component has a magnitude larger than said proximal component.

In some embodiments said compression force has a first magnitude wherein said proximal component is zero and said distal component is greater than zero, and wherein said compression force has a second magnitude applied after said first magnitude wherein said proximal component is greater than zero.

In some embodiments a liquid flow across said reaction region occurs in response to a combination of siphoning forces, surface tension forces and overpressure forces.

In some embodiments a liquid flow across said reaction region occurs primarily due to overpressure forces during a first time period, and primarily due to siphoning forces during a second time period subsequent to said first time period.

In some embodiments said internal chamber is further shaped and dimensioned to crumple said remainder portion of said strip including a section of said at least one sample pad, thereby forcing an amount liquid out of said at least one sample pad.

In some embodiments said internal chamber is further shaped and dimensioned to include a receptacle oriented to capture the distal tip of said strip therein.

In some embodiments said conjugate pad has a thickened shape having a wider cross-sectional dimension than said sample pad.

In some embodiments said strip is an immunochromatographic assay strip.

In some embodiments there is provided a device for testing a liquid sample for the concentration of an analyte, wherein said device comprises: at least one liquid sample testing strip comprising: at least one upstream conjugate pad including a source of mobilizable labeled first affinity binding members bindable to said analyte; and, a liquid permeable reaction region including at least one downstream result zone including immobilized second affinity capture binding members bindable to said analyte; a cartridge carrying said strip, wherein said cartridge comprises: a movable compression structure adapted to progressively compress said conjugate pad in a downstream direction.

In some embodiments there is provided that in a device for testing a liquid sample for the concentration of at least one analyte, wherein said device comprises a cartridge carrying at least one test strip having a sample pad, an upstream conjugate pad including a source of mobilizable labeled first affinity binding members bindable to said analyte; and, a downstream liquid permeable reaction region including a result zone including immobilized second affinity capture binding members bindable to said analyte; an improvement which comprises a compression structure associated with said cartridge, said compression structure shaped, dimensioned and located to impart a progressively downstream compression force upon said conjugate pad.

In some embodiments there is provided the combination of a strip-carrying cartridge and at least one test strip for testing a liquid sample for the concentration of at least one analyte, said strip comprising: at least one sample pad; at least one conjugate pad including a source of mobilizable labeled first affinity binding members bindable to said analyte; and, a liquid permeable membrane including at least one result zone including immobilized second affinity capture binding members bindable to said analyte; said cartridge comprising: a cartridge body, made of liquid impermeable material, having an internal cavity shaped and dimensioned to carry a first portion of said strip including said at least one conjugate pad; an end cap shaped and dimensioned to engage said body, made of liquid impermeable material, having an internal chamber shaped and dimensioned to enclose a remainder portion of said strip including a section of said at least one sample pad; a survey window though said body for reading a status of said at least one result zone; wherein said body comprises a compression structure shaped, dimensioned and located to impart a compression force upon said conjugate pad.

In some embodiments there is provided a method for conducting a liquid flow immunoassay for at least one analyte, wherein said method comprises: selecting an immunochromatographic strip comprising at least one sample pad, at least one conjugate pad including a source of mobilizable labeled first affinity binding members bindable to said analyte, and at least one result zone including immobilized second affinity capture binding members bindable to said analyte; depositing a liquid sample onto said at least one sample pad; allowing said sample to flow from said sample pad into said conjugate pad to a source of mobilizable binding members conjugated to a label, and specific to said analyte to form a labeled sample; compressing said conjugate pad to force a flow out of said conjugate pad and into said result zone; and, reading a quantitative result from said zone.

In some embodiments said compressing comprises passing said flow through a strip hugging passageway along said reaction region surrounding a cross-sectional perimeter of said strip between said conjugate pad and said result zone.

In some embodiments said label is colloidal gold.

In some embodiments the method further comprises moving said mixture downstream along a surface of a immunochromatographic assay strip under the combined forces of overpressure, and siphoning.

The language of the original claims below is incorporated by reference here as detailing various embodiments of the invention.

BRIEF DESCRIPTION OF THE DRAWINGS

FIG. 2 is a diagrammatical cross-sectional side view of the cartridge of FIG. 1 taken along line 2-2 shown in the cap open position.

FIG. 3 is a diagrammatical cross-sectional side view of the cartridge of FIG. 2 taken along line 3-3 showing the strip-enclosing constriction structure.

FIG. 4 is a diagrammatical cross-sectional side view of the strip of FIG. 2.

FIG. 5 is a diagrammatical cross-sectional side view of the cartridge of FIG. 1 shown in the cap closed position.

FIG. 9 is a diagrammatical cross-sectional side view of an alternate embodiment of a cap having a strip crumpling structure.

FIG. 10 is a diagrammatical cross-sectional side view of an alternate embodiment of a cartridge having a support shelf for supporting the free end of the strip.

FIG. 11 is a diagrammatical cross-sectional side view of an alternate embodiment of a cap having an internal deflectable beam progressive compression structure.

FIG. 12 is a diagrammatical cross-sectional side view of an alternate embodiment of a cap having an internal slider progressive compression structure.

FIG. 13 is a diagrammatical cross-sectional side view of an alternate embodiment of a cap having a pressurizing collapsible bulb progressive compression structure.

DESCRIPTION OF THE EXEMPLARY EMBODIMENTS

Figure 1:
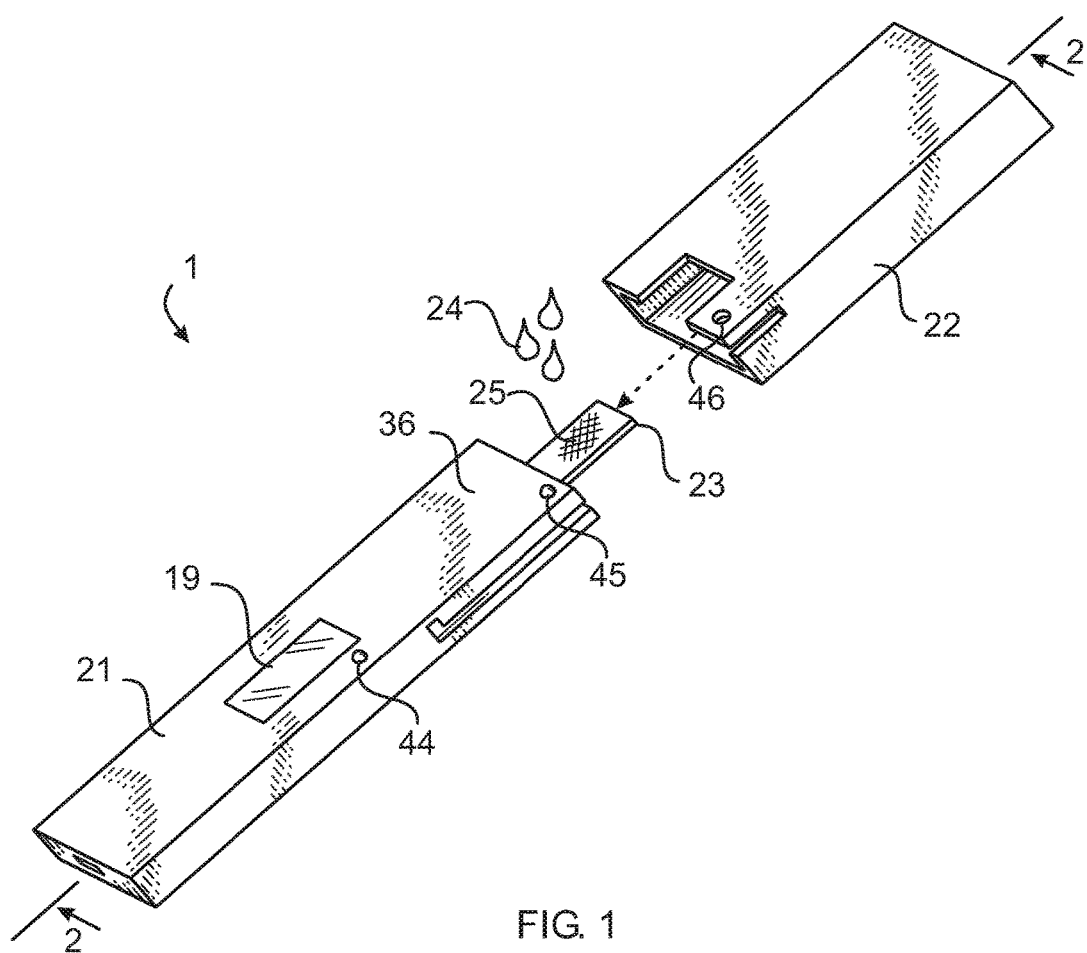
FIG. 1 is a diagrammatical perspective view of an assay cartridge according to an exemplary embodiment of the invention.

The instant embodiments are useful to rapidly determine the presence of an analyte in a liquid sample at a concentration which confirms the condition being tested. The sample can include, for example, body fluids such as whole blood, serum, plasma, urine, spinal fluid, amniotic fluid, mucous, saliva, and the like, or other fluids used in certain food and environmental testing.

The term "analyte", as used herein, refers to a compound or composition to be measured. The analyte can be any substance, such as an antigen or ligand, for which there exists a naturally or genetically occurring specific binding member such as a binding molecule, such as an antibody or receptor, and other molecules that exhibit the so-called "lock-in-key" pairing function.

Analyte also includes any antigenic substances, haptens, antibodies, and combinations thereof. The analyte can include a protein, a peptide, an amino acid, a ligand, a hormone, a steroid, a vitamin, a drug including those administered for therapeutic purposes as well as those administered for illicit purposes, a pathogen, and an exogenious infectious microbe such as a bacterium, a virus, and metabolites of or antibodies to any of the above substances. The analyte can also comprise an antigenic marker or antibody or receptor The precise nature of a number of analytes together with a number of examples thereof are disclosed in Litman, et al., U.S. Pat. No. 4,299,916, issued Nov. 10, 1981; and Tom, et al., U.S. Pat. No. 4,366,241, issued Dec. 28, 1982, each of which is hereby incorporated by reference in its entirety.

The signal provided to the user of the device is provided by accumulation of a visually detectable label conjugated to a mobilizable binding member such as a specific antibody and/or antigen; ligand and/or receptor. This mobilizable binding member is sometimes referred to as a "binding member molecule", "a first affinity binding member", "labeled binding member" or simply "conjugate". In the instant embodiments, labels that produce a readily detectable signal are used. Thus, the instant embodiments provide colored labels which permit visible detection of the assay results without the addition of further substances and/or without the aid of instrumentation.

The strips described in these embodiments can include regions or pads that may comprise dry porous material. By "porous" it is meant that the matrix of material forming the porous structure allows liquids to flow through it.

As used herein, the term "sample pad" means the part of the assay device which is in direct contact with the liquid sample first during test operation, i.e., it receives the sample to be tested for the analyte in question. The sample pad is made of porous material, such as porous paper, cotton, cellulose, mixed fibers, glass fiber, polyester fiber, and the like, such that the liquid sample can migrate, via liquid flow, from the sample pad toward the absorbent pad. The sample pad can be in lateral liquid flow contact with the conjugate pad by either an overlap or end-to-end connection. The term "conjugate pad" as used herein refers to the part of the assay device which is in liquid flow contact with the porous material of sample pad and the novel diffusive interrupting pad. The contact can be an overlap or end-to-end connection, such that the liquid sample can migrate via wicking action or by surface tension-based forces such as capillary forces from the sample pad through the conjugate pad to the interrupting pad. The conjugate pad comprises a porous material and a mobilizable labeled reagent that is capable of binding the analyte in question to form a labeled reagent-analyte complex which then migrates via liquid flow with the liquid sample to the interrupting pad.

The term "mobilizable" as referred to herein means diffusively or non-diffusively attached, or impregnated. The mobilizable reagents are capable of dispersing with the liquid sample and carried by the liquid sample in the liquid flow.

The exemplary embodiments will be described in connection with the detection of human immunodeficiency virus ("HIV") in a fluid specimen such as saliva as a putative target analyte. Those skilled in the art will readily appreciate adaptation of these embodiments to detect other analytes indicative of other pathogens, or pathogenic conditions in body, drugs of abuse ("DOA"), food or environmental fluid specimens.

Further the exemplary embodiments will be described in connection with an immunochromatographic assay based on antigen/antibody binding. Those skilled in the art will readily appreciate adaptation of these embodiments to other types of molecular affinity binding-based tests.

Referring now to the drawing, there is shown in FIGS. 1-5 a diagrammatical illustration of a labeled molecular affinity binding test device 1 including a cartridge body 21 and a cap 22 made from a generally liquid impermeable durable material such as injection molded plastic. The cartridge carries in an internal cavity at least one test strip 23 containing the chemicals necessary to conduct the labeled molecular affinity binding test. The strip has an oblong backing 15 made from liquid impermeable material such as plastic extending the entire length of the strip so that liquid can ride along the upper surface of the backing during its flow. The internal cavity of the cartridge body is shaped and dimensioned to carry a first portion 17 of the strip including the conjugate pad 26 impregnated with a lyophized, mobilizable, first affinity binding member such as an HIV antigen or antibody, conjugated to a label such as colloidal gold, and a reaction region 27 including one or more zones 28,29 impregnated with lyophized, immobilized, second affinity binder members intended to capture first affinity bound molecules. Thus the first affinity binding members are initially separated from the second affinity binding members.

The cap 22 can be shaped and dimensioned to engage the cartridge body, and have an internal chamber shaped and dimensioned to enclose a second, remainder portion 16 of the strip including the exposed end of the sample pad 25.

The device can be delivered in a preused condition where the strip has been preloaded into the cartridge and the cap protectively placed over the free end of the strip and held in place by a nib 45 on the cartridge engaging a hole 46 in the cap.

To initiate a test, the user removes the cap 22 so that the device is in the cap open position as shown in FIG. 1, and deposits a liquid sample 24 upon the sample pad 25 at a distal exposed end of the strip 23. The sample liquid then flows primarily through the forces of capillarity and gravity into a thickened, convexly-shaped conjugate pad 26. The liquid will tend toward fully saturating the thickened conjugate pad before any substantial flow leaves the conjugate pad for the reaction region 27.

The thickened conjugate pad 26 is located beneath a compression structure 36 on the cartridge body 21. The compression structure can be formed by a cantilevered beam 38 having a fixed proximal end and a distal free end 42. The beam is allowed to deflect downwardly as it comes into contact with the sloped surface of the ramp 32. The downward deflection is facilitated by a narrow isthmus of material 37 connecting the fixed proximal end of the beam to the cartridge body. The isthmus acts as a relatively stiff mechanical hinge providing predetermined resistance to deflection which can be selected during manufacture by selecting the thickness of the isthmus. This helps the beam from being inadvertently deflected prior to the directed intentional placement of the cap.

The user then replaces the cap 22 and forces it into the cap closed, test initiation position shown in FIG. 5. A second nib 45 engages the hole 46 on the cap to indicate that the cap has reached the closed position. The sloped surface of the ramp 32 of the cap having an angle 33 of between about 0 and 25 degrees progressively forces the cantilevered beam of the compression structure 36 downward as the cap moves toward the closed position. The beam presses against the top side of the thickened conjugate pad 26 forcing liquid out of the pad due to an overpressure force an on downstream as indicated by the arrow 47 toward the reaction region 27 carrying one or more result zones 28,29 of immobilized, second affinity binding members. The analyte molecules already bound to conjugated first affinity binding members can now bind to the immobilized members located in the zones and accumulate there in significant numbers to indicate a test result through the observation window 19.

Liquid continues to flow into an absorbent reservoir pad 30 located at the proximal end of the cartridge. An empty chamber 31 having an opening 39 outside the cartridge at the proximal end of the cartridge relieves any build up of backwards pressure against the flow of liquid into the reservoir. Optionally, the chamber can have an opening to the outside to ensure no build up of pressure occurs during the movement of liquid through the device. Optionally, an amount of dessicant can be placed in the chamber to keep the strip dry until use.

As shown in FIG. 3, it is important to note that the reaction region 27 part of the strip 23 is surrounded on its perimeter 35 by a strip-enclosing constriction structure formed by the close proximity of the cartridge body 21 so that once liquid has reached the reservoir 30, additional liquid is drawn out of the conjugate pad by siphoning forces in combination with the other forces. This siphoning force takes over for a diminishing compression force as the beam reaches its full deflection, so that the pressure of the liquid flow is maintained. The sample pad, conjugate pad, reaction region, and absorption pad are in direct liquid flow contact with each other such that the direction of liquid flow in the test device is from the sample pad to conjugate pad to reaction region and ultimately to the absorption pad. Thus, the liquid sample is driven through the strip by a force which is the combination of forces due primarily to compression forces and siphoning, and potentially gravity.

Figure 6:
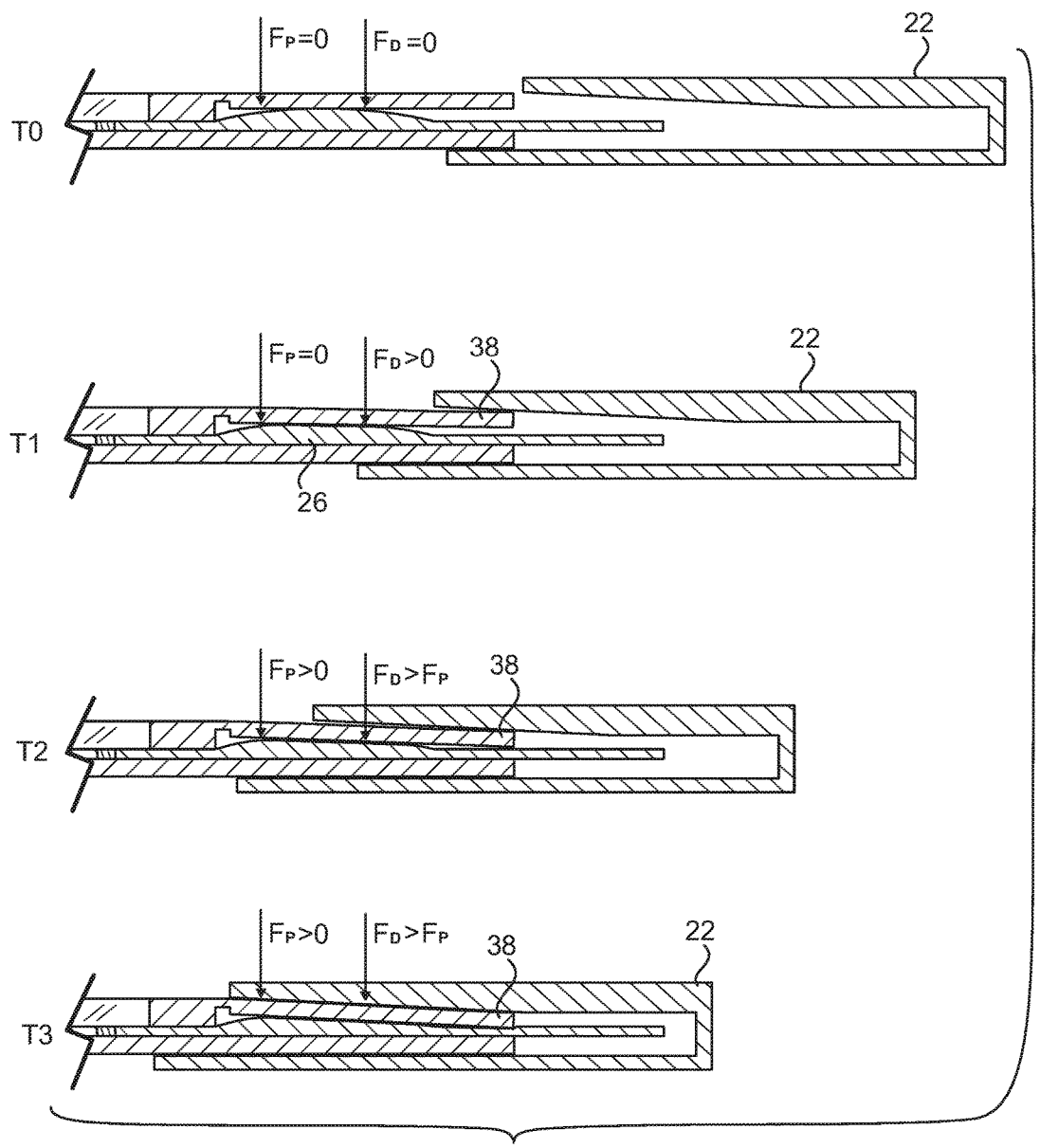
FIG. 6 is a diagrammatical cross-sectional side view of the cartridge of FIG. 1 showing progressive compression force components at various times and position during cap emplacement.
Figure 7:
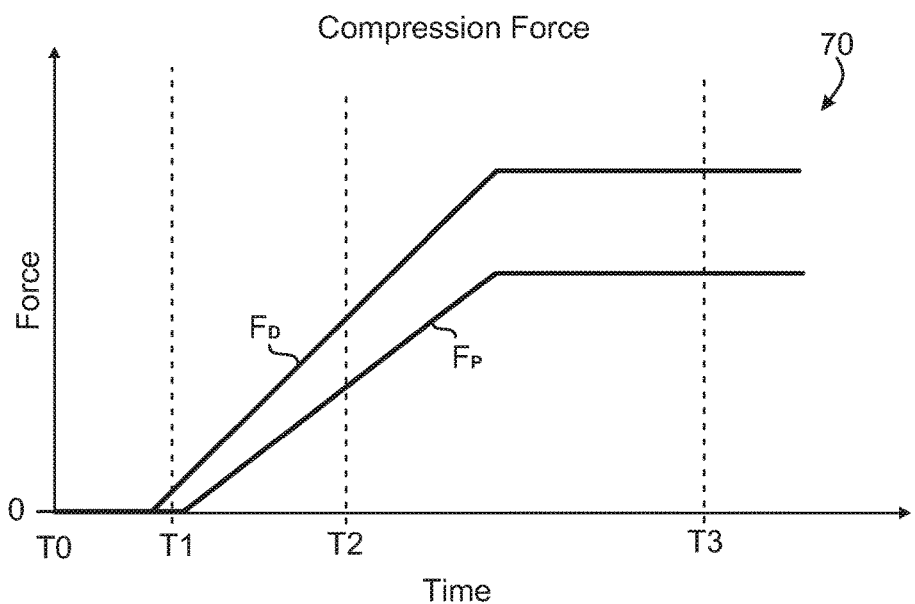
FIG. 7 is a diagrammatical chart showing progressive compression force components at various times during cap emplacement.

As shown schematically in FIG. 6 and graphically in FIG. 7, the compression force 70 is applied progressively along the downstream direction 47 of liquid flow during cap emplacement onto the cartridge body. Before the cap 22 contacts the cartridge body 21 at T0 there is no compression force applied. At time T1 when the cap 22 has been moved more proximally, the deflecting the beam 38 generates a compression force having a force component Fd applied to a distal point on the conjugate pad 26 that is greater than zero while the force component Fp at a proximal point remains zero. At time T2 as the compression structure beam 38 becomes more deflected, a compression force is applied having a force component Fp applied to the proximal point on the conjugate pad 26 that is greater than zero, while the force component Fd at the distal point is greater than Fp. At time T3 when the compression structure beam 38 is fully deflected and the cap 22 is in the closed position, a compression force is applied having a force component Fp and Fd at their maximums, where distal point Fd remains greater than Fp.

Figure 8:
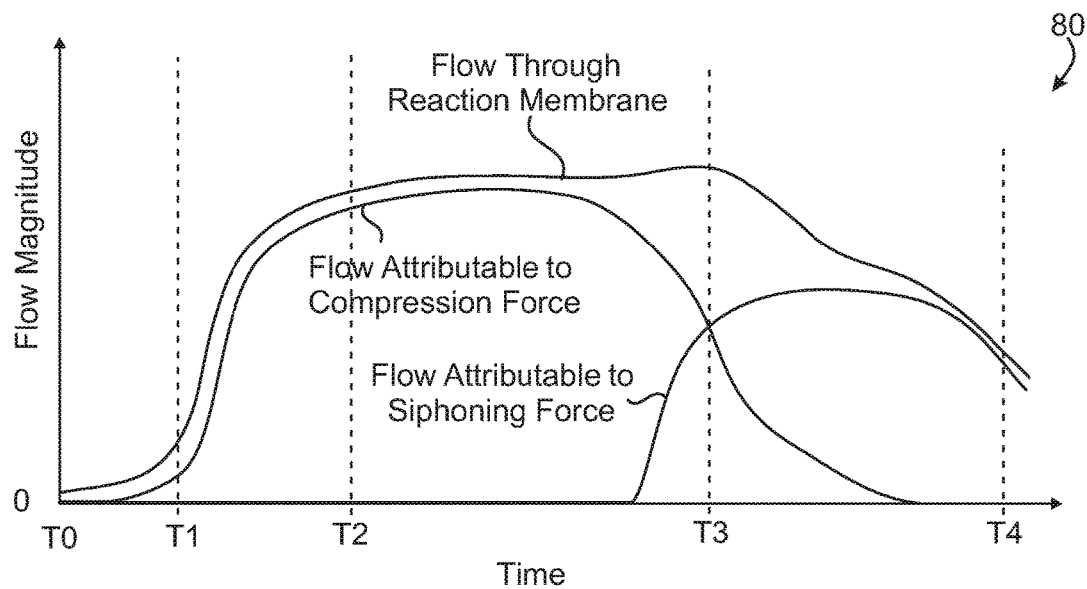
FIG. 8 is a diagrammatical chart showing the relatively uniform flow magnitude during a transition from primarily a compression driving force to a siphoning driving force.

As graphically shown in FIG. 8, the magnitude of the flow through the reaction region over time 80 is at T0 first attributable to surface tension forces (also known as capillarity) alone while the cap remains in the open position. Then as the cap is replaced from T1 to T3 the overall flow through the reaction region is primarily attributable to the compression force. After the cap has been replaced, the flow attributable to the compression force drops off, while the flow attributable to siphoning increases. By T4 the flow is almost entirely driven by siphoning. In this way, the magnitude of the flow through the reaction region is more uniform over a longer period of time because the flow occurs primarily due to overpressure forces during a first time period, and primarily due to siphoning forces during a second, subsequent time period.

Referring now to FIG. 9 there is shown an alternate embodiment of the progressive compression structure. The cap 62 similar to the device of FIG. 1 includes an additional angled bulkhead 63 for directing the distal end 64 of the strip 65 toward a receptacle 66 as the cap is moved from the open position to the closed position. Once the distal end of the strip is trapped in the receptacle, the bulkhead forces the end of the strip crumple upon itself into corrugations 67 which serve to drive liquid out of the sample pad and downstream into the conjugate pad. This added source of liquid can further pressurize the liquid exiting the conjugate pad. The strip crumpling structure can be used alone or in combination with other structures for driving liquid in a downstream direction on the strip.

Referring now to FIG. 10 there is shown an alternate embodiment of the cartridge body 91 having a support shelf 92 supporting the distal end 93 of the strip 94. Further, the top of the conjugate pad 95 is exposed. This cartridge body can be used with various progressive compression structures as detailed below.

In FIG. 11 there is shown an alternate embodiment of the progressive compression structure 101 having a deflectable beam 110 having a fixed end 111 secured to the distal end 112 of the cap 113. Once the cap is place in a closed position upon the cartridge body 91 the beam is located above the sample pad and the conjugate pad. Upon depressing a push button 114, the beam is deflected against the sample pad and the conjugate pad in a progressive compression action which forces liquid from the sample pad and conjugate pad toward the reaction region.

In FIG. 12 there is shown an alternate embodiment of the progressive compression structure 102 having a moveable slider 120 mounted within a track 121 on the cap 122. The slider has a shoe 123 which bears against the sample pad once the cap is placed in a closed position upon the cartridge body 91. Upon pushing the button of the slider proximally toward the proximal end of the cartridge, the shoe progressively imparts a compression force along the sample pad and then the conjugate pad of the strip which forces liquid from the sample pad and conjugate pad toward the reaction region. A protective, friction-reducing bib 124 made from a flexible liquid resistant material such as a pliable plastic separates the bottom of the shoe from the strip and facilitates the sliding of the shoe over the strip.

In FIG. 13 there is shown an alternate embodiment of the progressive compression structure 103 having a pressure inducing collapsible bulb 130 made from resiliently flexible, air-tight material such as rubberized plastic formed into the cap 131. Once the cap is placed in a closed position upon the cartridge body 91, an air-tight seal is formed with the cartridge body over the end of the strip and the air-filled chamber 132 inside the bulb is open to the end of the strip. The bulb can then be collapsed under the force of a person's finger and thumb to increase the pressure within the chamber imparting a force progressively from the exposed end of the strip at the sample pad and then on to the conjugate pad which forces liquid from the sample pad and conjugate pad toward the reaction region.

The application of the progressive compression force has a dramatic effect on micro-flow dynamics in the strip. In general the result is a more rapid and thorough mixing of the sample with the reaction molecules so that a greater and more rapid opportunity is provided for the first and second bindings to occur, and a more even liquid front reaching the sites of second affinity binding.

More specifically, the pressurized movement of the liquid sample through the porous material of the conjugate pad 26 causes the liquid front to separate into branches and rejoin from different directions as it courses around the material fibers. The convergence from different directions causes a mixing across the liquid front and the liquid that follows as the sample flows downstream 47. This enhanced mixing can cause the break-up of clumps of non-analyte molecules which may carry mobilizable labeled binding members, to reduce false positives. The mixing also reduces the differences in the concentrations of non-analyte molecules and labeled analyte complexes so that they are spread more evenly.

In addition, prior to the compression force being applied, the liquid has tended to saturate the thickened conjugate pad 26. Once the compression force is applied, the liquid forcefully exits the conjugate pad into a narrower cross-section of the strip entering the reaction region 27. This action increases the velocity of the liquid in the reaction region according to the Bernoulli Principle reducing its pressure causing further mixing and leading to a more evenly mixed liquid front. Further, because of the thickened shape of the conjugate pad, the direction of flow of the liquid exiting the upper parts of the conjugate pad must make a downward turn 48 to flow into the reaction region. This change in direction also serves to better mix the liquid.

Once the liquid front reaches the reaction region 27, the concentrations have superior uniformity across the width of the strip which leads directly to giving the labeled analyte complexes a greater opportunity to form the second affinity binding at the immobilized sites in the result zones 28,29 and thereby increasing the overall sensitivity and specificity of the test and reducing false negatives.

Figure 14:
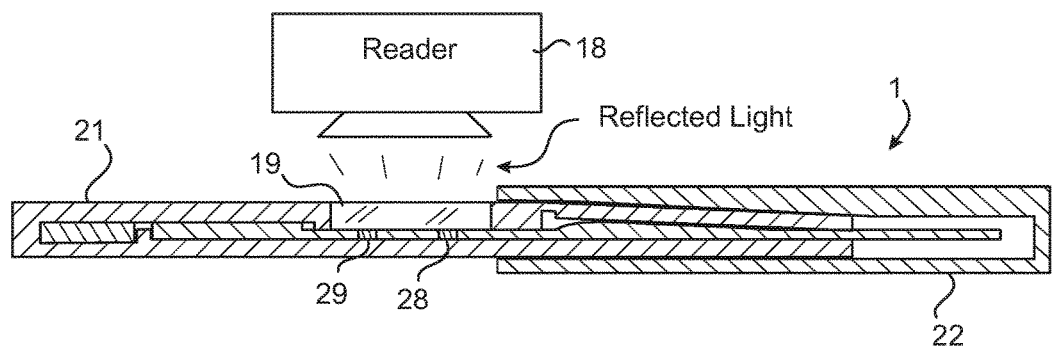
FIG. 14 is a diagrammatical cross-sectional side view of the cartridge of FIG. 1 loaded in a result reader.

Within 10 seconds or less a predicable amount of reactable sample liquid has passed through the conjugate pad and through the reaction region. This amount is about 100 to 300 microliter. As shown in FIG. 14, an automated reader 18 can read by reflected light the result of the test and generate an electronic signal that can be forwarded to a computer for further analysis and distribution to a data network. The computer can be implemented using a mobile phone device running the appropriate software as disclosed in Ozcan et al., supra. By being able to predict the amount of reacted sample that has passed through the reaction region, the intensity of the lines in the result zones can indicate a quantitative result. In other words, the automated reader can the detect not just whether a line has appeared or not, but rather the intensity of the line, and digitize that intensity reading. That reading corresponds directly with the amount of analyte present in the sample, providing a digitized quantitative result.

Figure 15:
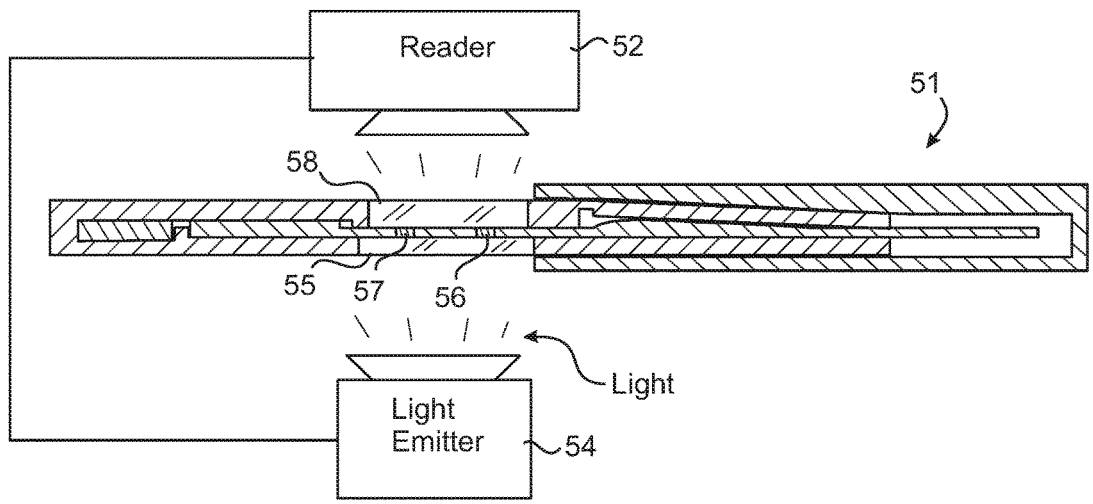
FIG. 15 is a diagrammatical cross-sectional side view of an assay cartridge according to an alternate exemplary embodiment of the invention having a light emitter enhanced reader.

Alternately, as shown in FIG. 15, a device 51 can include a second window 55 located beneath the result zones 56,57 so that a light emitter 54 can shine light through the reaction region to be received by the reader 52 and the mobile phone analysis tool 53. Indeed the entire cartridge can be made from translucent material.

The above device can within about 2 minutes provide a quantitative analysis of the presence of particular antigens or antibodies, and confirm the biochemical or pathogenic condition such as HIV infection, or early stage cancer prior to metastasis, or acute cardiac disorder, or the presence of abused drugs by way of a simple, inexpensive and disposable device that can be manipulated safely by a relatively low skilled person.

Depending on the disease being tested and the condition of the fluid specimen, many of the above embodiments have been found to achieve an accuracy of at least 99.99%.

The effect of gravity on the flow is made to be negligible.

In this way the device also directs the flow of liquids throughout the device under the pressure imparted by the compression structure upon the strip and in absence of any repetitive liquid pumping apparatus.

In addition, because a result is obtained so quickly, typically within 1 minute, the test does not require additional buffers or other methods to halt the reaction.

While the exemplary embodiments have been described, modifications can be made and other embodiments may be devised without departing from the spirit of the invention and the scope of the appended claims.

What is claimed is:

1. A method for conducting a liquid flow immunoassay for at least one analyte, wherein said method comprises:
   selecting an immunochromatographic strip comprising at least one sample pad, at least one conjugate pad including a source of mobilizable labeled first affinity binding members bindable to said analyte, and at least one result zone including immobilized second affinity capture binding members bindable to said analyte;
   depositing a liquid sample onto said at least one sample pad;
   allowing an amount of said sample to flow from said sample pad into said conjugate pad
   progressively compressing said conjugate pad to force a flow of said amount out of said conjugate pad and into said result zone; and,
   reading a result from said result zone.

2. The method of claim 1, which further comprises:
   carrying said immunochromatographic strip within a cartridge having a moveable beam cantilevered over said conjugate pad.

3. The method of claim 2, wherein said progressively compressing comprises:
   deflecting a beam onto said conjugate pad.

4. The method of claim 3, wherein said deflecting a beam comprises:
   progressively forcing a ramp structure against said beam.

5. The method of claim 3, wherein said deflecting a beam comprises:
   engaging an end cap upon said cartridge wherein said end cap comprises an internal ramp structure oriented to bear against said beam and force progressive deflection of said beam toward said conjugate pad during movement of said cap from a first position to a second position.

6. The method of claim 1, wherein said progressively compressing comprises:
   applying a distal compressive force component to a distal point on said conjugate pad; and,
   applying a proximal compressive force component to a proximal point on said conjugate pad, downstream from said distal point, wherein said distal compressive force component has a magnitude larger than said proximal compressive force component.

7. The method of claim 6, wherein said applying a distal compressive force component comprises orienting said distal compressive force component substantially orthogonal to a direction of said flow.

8. The method of claim 1, which further comprises:
   passing said flow through a strip hugging passageway surrounding a cross-sectional perimeter of said strip between said conjugate pad and said result zone.

9. The method of claim 1, which further comprises:
   moving said flow downstream along a surface of said immunochromatographic assay strip under the combined forces of overpressure, and siphoning.

10. The method of claim 1, wherein said reading a result comprises detecting a quantitative result.

11. A device for testing a liquid sample for the concentration of at least one analyte, wherein said device comprises:
    at least one test strip comprising:
       at least one sample pad;
       at least one conjugate pad including a source of mobilizable labeled first affinity binding members bindable to said analyte; and,
       a liquid permeable reaction region including at least one result zone including immobilized second affinity capture binding members bindable to said analyte;
    a cartridge body having an internal cavity carrying a first portion of said strip including said at least one conjugate pad;
    wherein said body comprises a compression structure oriented to impart a progressive compression force upon said conjugate pad.

12. The device of claim 11, wherein said body further comprises a constriction passageway along a part of said reaction region including said at least one zone;
    wherein said constriction passageway is shaped and dimensioned to loosely contact an entire perimeter of a latitudinal cross-section of said strip, thereby creating a liquid siphoning region including said at least one zone.

13. The device of claim 11, wherein said compression structure comprises a deflectable beam cantilevered over said conjugate pad; wherein said deflectable beam comprises a first end fixed to said body and a second free end.

14. The device of claim 13, wherein said device further comprises an end cap which comprises an internal ramp structure oriented to bear against said beam and force progressive deflection of said beam toward said conjugate pad during movement of said cap from an open position to a closed position.

15. The device of claim 11, wherein said compression force has a distal component and proximal component, downstream from said distal component, and wherein said distal component has a magnitude larger than said proximal component.

16. The device of claim 15, wherein said compression force has a first magnitude wherein said proximal component is zero and said distal component is greater than zero, and wherein said compression force has a second magnitude applied after said first magnitude wherein said proximal component is greater than zero.

17. The device of claim 11, wherein a liquid flow across said reaction region occurs in response to a combination of siphoning forces, surface tension forces and overpressure forces.

18. The device of claim 11, wherein a liquid flow across said reaction region occurs primarily due to overpressure forces during a first time period, and primarily due to siphoning forces during a second time period subsequent to said first time period.

19. The device of claim 11, wherein said internal cavity is further shaped and dimensioned to crumple said remainder portion of said strip including a section of said at least one sample pad, thereby forcing an amount liquid out of said at least one sample pad; and,
    wherein said internal cavity is further shaped and dimensioned to include a receptacle oriented to capture the distal tip of said strip therein.

20. A device for testing a liquid sample for the concentration of an analyte, wherein said device comprises:
    at least one liquid sample testing strip comprising:
        at least one upstream conjugate pad including a source of mobilizable labeled first affinity binding members bindable to said analyte;
        said conjugate pad including a distal point and a proximal point; and,
        a liquid permeable reaction region including at least one downstream result zone including immobilized second affinity capture binding members bindable to said analyte;
    a cartridge carrying said strip, wherein said cartridge comprises:
        a movable compression structure adapted to progressively compress said points of said conjugate pad in a downstream direction.

* * * * *